United States Patent [19]
Lau et al.

[11] Patent Number: 5,812,255
[45] Date of Patent: Sep. 22, 1998

[54] PROCESS AND DEVICE FOR DETERMINING THE REFRACTIVE INDEX OF DIFFERENT MEDIUMS

[76] Inventors: Matthias Lau, Blasewitzer Strasse 22, Dresden, Germany, D-01307; Uwe Kirschner, Altrachau 41, Dresden, Germany, D-01139

[21] Appl. No.: 765,955
[22] PCT Filed: Jul. 13, 1995
[86] PCT No.: PCT/DE95/00910
  § 371 Date: Jan. 10, 1997
  § 102(e) Date: Jan. 10, 1997
[87] PCT Pub. No.: WO96/02822
  PCT Pub. Date: Feb. 1, 1996

[30] Foreign Application Priority Data

Jul. 13, 1994 [DE] Germany ............ 44 24 628.5

[51] Int. Cl.[6] .................. G01N 21/41; G01N 33/487; G01N 21/75
[52] U.S. Cl. ................ 356/128; 356/136; 356/445
[58] Field of Search ................. 356/128, 135, 356/136, 445

[56] References Cited

U.S. PATENT DOCUMENTS

| | | |
|---|---|---|
| 4,595,833 | 6/1986 | Sting . |
| 4,699,511 | 10/1987 | Seaver ........................ 356/136 |
| 5,245,410 | 9/1993 | Yuste et al. ............... 356/445 |
| 5,359,681 | 10/1994 | Jorgenson et al. ............ 385/12 |

FOREIGN PATENT DOCUMENTS

| | | |
|---|---|---|
| 0209489 | 1/1987 | European Pat. Off. . |
| 0326291 | 2/1989 | European Pat. Off. . |
| 0409033 | 1/1991 | European Pat. Off. . |
| 0410505 | 1/1991 | European Pat. Off. . |
| 3726412 | 2/1989 | Germany . |
| 4010949 | 10/1991 | Germany . |
| 4305830 | 8/1994 | Germany . |
| 669050 | 2/1989 | Switzerland . |
| 681920 | 6/1993 | Switzerland . |
| 2192070 | 12/1987 | United Kingdom . |

OTHER PUBLICATIONS

Maria et al., "Fiber–Optic Sensor Based on Surface Plasmon Interrogation," *Sensors and Actuators B*, Bd.B12, No. 3, pp. 221–223, (Apr. 1993).

Abauf et al., "Optical Probe for Local Void Fraction and Interface Velocity Measurements," Bd. 49, No. 8, pp. 1090–1094 (1978).

Spindler et al., "Faseroptischer Sensor zur Messung des örlichen Gasgehaltes in Flüssigkeiten," *Technisches Messen tm*, 54, pp. 50–55 (1989).

Schlemmer et al., "ATR technique for UV/VIS analytical measurements," *Frese–nuis Z. Anal. Chem.*, 329, pp. 435–439 (1987).

Jorpensen et al., "Control of the Dynamic Range and Sensitivity of a Surface Plasmon Resonance Based Fiber Optic Sensor," *Sensors and Actuators B*, Bd.A43, No. 1/3, pp. 44–48, (Jun. 1994).

Jorgenson et al., "A Fiber–Optic Chemical Sensor Based on Surface Plasmon Resonance," *Sensors and Actuators B*, Bd.12, No. 3, pp. 213–220, (Apr. 1993).

*Primary Examiner*—Richard A. Rosenberger
*Attorney, Agent, or Firm*—Greenblum & Bernstein P.L.C.

[57] ABSTRACT

The proposed fibre-optic sensor is based on surface plasmon resonance and consists of a monomode fibre with multiple angled facets at its end face and suitable coatings. A first partial face is preferably metal-coated, a second is provided with a conventional detection layer, and the angle between the two partial surface is 30°, 45° or 90°.

10 Claims, 3 Drawing Sheets

PROCESS AND DEVICE FOR DETERMINING THE REFRACTIVE INDEX OF DIFFERENT MEDIUMS

BACKGROUND OF THE INVENTION

1. Field of the Invention

The invention relates to a Process and to a device for carrying out the Process, by means of which the refractive index of various media can be measured. For this purpose there is utilised the excitation of surface plasmons in a boundary layer metallic dielectric and the close dependence of the resonance conditions on the refractive index of the layer or of the coating system adjoining the metallic layer. The invention relates in particular to the emission and derivation of signals by fibre optics. Possible applications of the invention lie in the construction of fibre-optic sensors for measuring physical, chemical and biological magnitudes, which may be indirectly detected through an alteration in refractive index.

2. Description of Background Information

Fibre optic SPR sensors have been intensively investigated for some years. The first attempts (EP-PS 0 410 505) proceeded in this respect from the conventional Kretschmann arrangement with a solid glass prism, to multi-mode fibres being used for coupling and decoupling the monochromatic light. The intensity of the radiation reflected at the receiving fibre is measured, the operating point being set by displacement of this fibre.

A sensor is known from the publication "Fibre-optic sensor based on surface plasmon interrogation", Letizia De Maria, et. al. Sensors an Actuators B, 12 (1993) 221–223, which uses the obliquely-ground and coated end face of a mono-mode fibre as a sensor head.

Here also operation was with monochromatic light from a He-Ne-laser and the polarisation was set by means of a rotating λ/2 delay plate. The sinusoidal signal arising at the detector has a minimum and a maximum, as the surface plasmons are only excited by the TM-wave, whereas the TE-wave serves as a reference signal. Precise measurement in this arrangement requires optimum polarisation and a high degree of stability of the wavelength. A disadvantage in this case is the necessary mechanical system for rotation of the λ/2 plate and the low intensity diffused back by the sensor head.

A further SPR-sensor with a glass fibre is known from EP-PS 0 326 291, in which however the fibre-optic derivation of the signal obtained is not possible.

A fibre-optic SPR-sensor proposed in DE-PS 43 05 830 is adjustable only with difficulty due to the use of two fibres for exciting and retroreflection of the coupled light.

A further SPR-sensor on the basis of monomode fibres is described in New "in-line" optical-fibre sensor based on surface plasmon excitation, R. Alonso, F. Villuendas, J. Tornos and J. Pelayo, Sensors and Actuators A, 37–38 (1993) 187–192. In this case excitation of the surface plasmon resonance is effected with a thin gold layer (15–35 nm) on the ground periphery of a monomode fibre embedded in an epoxy resin.

Here also linearly polarised, monochromatic light is coupled into the fibre and the transmission is evaluated as a measurement magnitude.

Due to the use of coherent sources and the necessary stabilisation of wave length, good-value sensors are difficult to manufacture in this variant.

In the publication A Novel Surface Plasmon Resonance based Fiber Optic Sensor Applied to Biochemical Sensing, R. C. Jorgenson et. al., SPIE VOL. 1886 (1993), p. 35–48, the vapour-coated cylinder surface of the core of a multi-mode glass fibre serves to excite surface plasmons with broad-band light. The signal reflected at the point of the fibre is analysed with the aid of a spectrometer. The wavelength of the damping maximum is in this case a measure for the refractive index of the medium adjoining the metallic layer. A serious disadvantage of this arrangement resides in the intense propagation of the resonance due to the number of modes, and thus the multiple excitation of surface plasmons at different wavelengths.

The object of the invention is to propose a fibre-optic SPR-sensor which is favourable in terms of energy and which is suitable for use with multi-mode fibres, without accepting the disadvantageous propagation of the resonance due to a plurality of different modes.

This object is achieved according to the invention by a process as defined in claim 1. The device according to the invention is the subject-matter of claim 2.

Further preferred developments of the invention are the subject-matter of the sub-claims.

The process according to the invention for exciting surface plasmon resonance is advantageously suitable for emission and derivation of signals by means of optical fibres. In particular when multi-mode fibres are used along with broad-band light, good-value sensors may potentially be produced. In this respect progress in the development of miniaturised spectrometers, for example in LIGA technology, was considered. In comparison to vapour coating of the cylinder surface, by means of the arrangement due to the invention a narrower resonance was achieved due to the possible radiation collimation through corresponding lenses. It is possible, in the further developments of the arrangement with planar terminal surface portions, by using a polarisation filter, to exclude the TE-wave, so that the intensity of reflected light of the resonant wavelength can come to 0%.

A particular advantage of variants which operate without mono-mode fibres or coherent sources, resides in good-value components and low sensitivities to fluctuations in wave length.

Further advantages, features and possible applications of the present invention will become apparent from the following description in conjunction with the drawings, which show:

DETAILED DESCRIPTION OF THE DRAWINGS

Figure 1A:
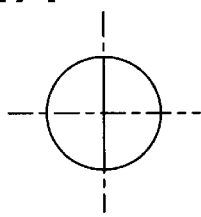
FIG. 1A depicts an end view of the end surface of FIG. 1.
Figure 1:
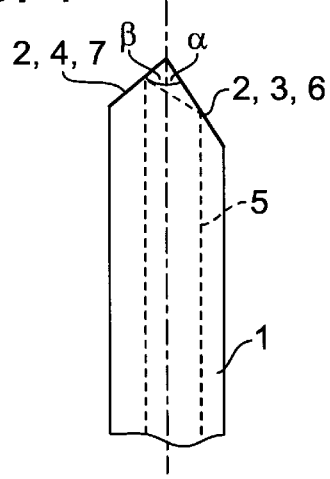
FIG. 1 depicts the end surface of an optically transparent body with two planar, oblique partial surfaces.
Figure 5:
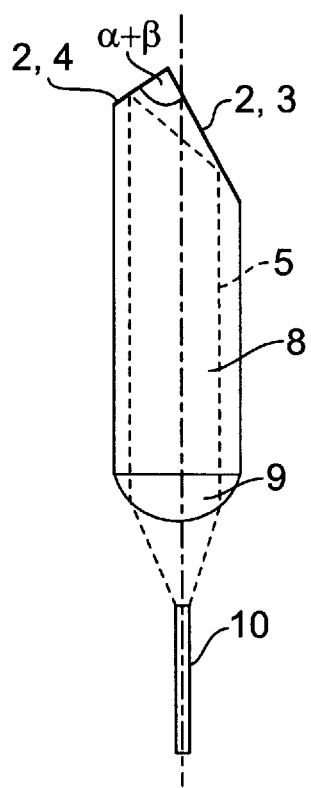
FIG. 5 depicts a diagrammatic view of the sensor head.

As can be seen from FIGS. 1 and 5, light 5 impinging parallel to the axis of an optically transparent cylinder 1' is reflected from a plurality of partial surfaces 3, 4 of the machined end surface 2 in such a way that, after at least two reflections, it is returned again parallel to the axis in cylinder 1, surface plasmons being excited by angle and wavelength used in at least one reflection. First partial surface 3 is inclined at an angle a with respect to the longitudinal axis of cylinder 1 and includes an SPR-exciting layer or coating 6. Second partial surface 4 is inclined at an angle β with respect to the longitudinal axis of cylinder 1. The second partial surface 4 serving for reflection can, if this is of advantage in manufacturing terms, be coated with the same coating system 7, if the SPR-metal layer has a sufficiently high reflection coefficient. As shown in FIGS. 1 and 5, angles α+β+90°.

The cylindrical body 1 can in this respect for example be a glass rod, a bar lens, a GRIN lens or also an optical fibre. The material used must be transparent for the wavelength used.

Figure 2A:
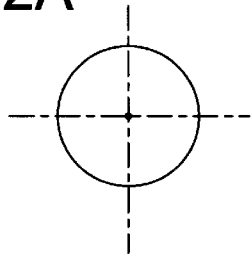
FIG. 2A depicts an end view of the end surface of FIG. 2.
Figure 2:
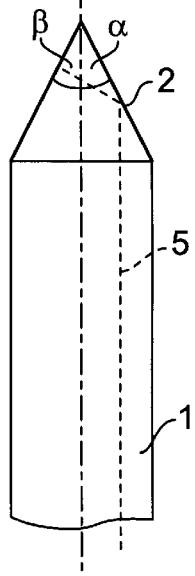
FIG. 2 depicts the end surface of an optically transparent body with conically-shaped end surface.
Figure 3A:
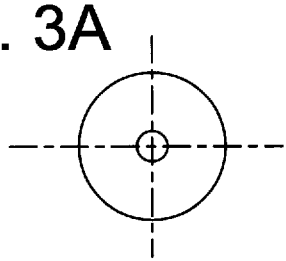
FIG. 3A depicts an end view of the end surface of FIG. 3.
Figure 3:
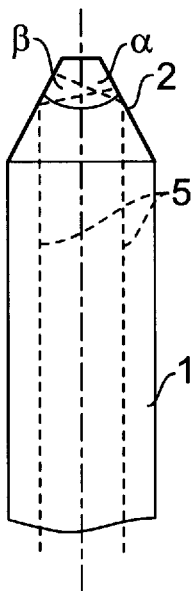
FIG. 3 depicts the end surface of an optically transparent body with a truncated-conical end surface.

FIG. 2 depicts the machined end surface 2 as having a conical configuration, and where one side of the conical surface (or partial surface) is inclined at an angle α with respect to the longitudinal axis of cylinder 5, and the opposite side surface (or partial surface) is inclined at an angle β to the longitudinal axis. In this instance it can be seen that α=β=30°. FIG. 3 depicts the machined end surface 2 as having a frustoconical configuration, and where the angles α and β of the opposite side surfaces (partial surfaces) have the same relationship as those of FIG. 2.

In the example according to FIG. 5 the end surface 2 of a bar lens 8 is so machined that two planar partial surfaces 3, 4 results, which enclose an angle α=β=90°; the angles α and β may be equal to 45°, although this embodiment is not depicted in the drawings. Thus the intersecting straight line of the partial surfaces 3, 4 lies vertically to the cylinder axis 1.

At the other end there is located in the focal point of the convex lenses 9 at the other end of the cylinder 1 in the extension of the cylinder axis, the end surface of a multi-mode fibre 10, which serves to emit and derive broad-band light 5.

Figure 4:
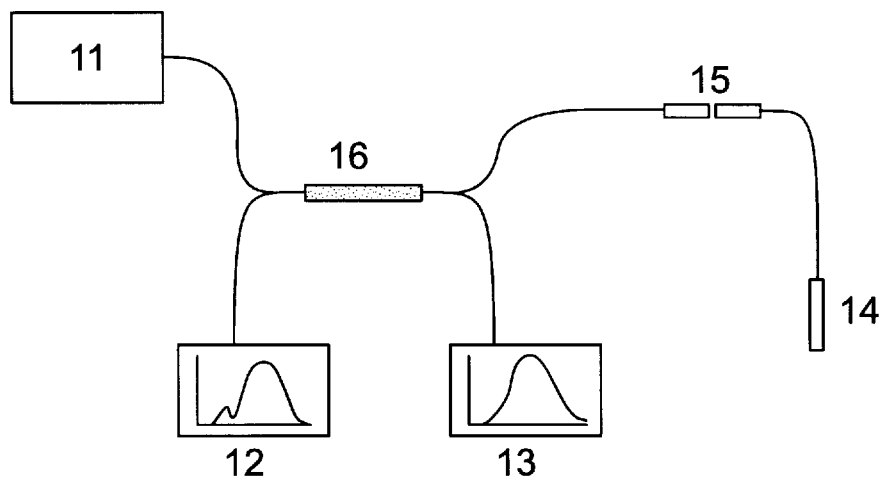
FIG. 4 depicts circuit diagram of the triggering and evaluation unit given by way of example.

FIG. 4 shows in diagrammatic form a possible optoelectronic system for evaluating the sensor signal.

The supply lines to source 11, spectrometer 12, 13 and sensor head 14 via a plug-in connection 15 are connected to an X-coupler 16. The spectrometers 12, 13 serve to obtain the sensor signal and a reference signal for calculating the source spectrum.

We claim:

1. A process for determining the refractive index of different mediums, in which chemical, physical and biological magnitudes are detectable by surface plasmon resonance (SPR) by using an optical beam coupled into a cylindrical body having a longitudinal axis and transparent to the optical beam, comprising:

passing said coupled optical beam into the cylindrical body;

reflecting the coupled optical beam, by at least two reflections, from an end surface of the cylindrical body to a coupling and de-coupling point, via at least two partial surfaces inclined toward one another at the end surface, the at least two partial surfaces being inclined at an angle with respect to the longitudinal axis of the cylindrical body; and, exciting surface plasmon resonance at the end surface by said optical beam, said surface plasmon resonance being excited at least during one such reflection, at a wavelength of the optical beam.

2. A device for use in determining the refractive index of different mediums by surface plasmon resonance (SPR), comprising:

an optically transparent cylindrical body having a longitudinal axis and an end surface forming at least two partial surfaces, said at least two partial surfaces being inclined at an angle with respect to the longitudinal axis of said cylindrical body, and wherein said at least two partial surfaces includes a first partial surface inclined at an angle (α) towards the longitudinal axis of the cylindrical body; and, at least one of said at least two partial surfaces having an SPR-exciting layer or layer system formed thereon.

3. Device according to claim 2, wherein said at least two partial surfaces include a second partial surface inclined at an angle (β) with respect to the longitudinal axis of the cylindrical body, and each said partial surface being selected from one of a reflective surface and a surface provided with a coating exciting surface plasmon resonance.

4. Device according to claim 3, characterised in that the sum of the angles α and β comes to 90°.

5. Device according to claim 3, wherein said at least two partial surfaces are formed by portions of one of a conical and a frustoconical end surface of said cylindrical body.

6. Device according to claim 5, wherein the angles α and β are equal to 30°.

7. Device according to claim 3, wherein the angles α and β are equal to 45°.

8. Device according to claim 2, wherein said cylindrical body is a cylindrical light-wave guide in the form of an optical fiber or a bar lens.

9. Device according to claim 2, wherein the optical beam may be coupled and decoupled via one of an external optical lens, a lens integrated in the cylindrical body and an optical system.

10. Device according to claim 2, further comprising a polarization filter to exclude the TE-wave component.

* * * * *